United States Patent
Ooi et al.

(10) Patent No.: US 11,793,481 B2
(45) Date of Patent: Oct. 24, 2023

(54) ULTRASONIC DIAGNOSTIC APPARATUS AND BODY MARK DISPLAY METHOD

(71) Applicant: CANON MEDICAL SYSTEMS CORPORATION, Otawara (JP)

(72) Inventors: Nobuhide Ooi, Nasushiobara (JP); Takashi Masuda, Utsunomiya (JP); Asuka Ozawa, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 17/225,278

(22) Filed: Apr. 8, 2021

(65) Prior Publication Data

US 2021/0315540 A1    Oct. 14, 2021

(30) Foreign Application Priority Data

Apr. 9, 2020  (JP) ................................ 2020-070295

(51) Int. Cl.
| | |
|---|---|
| *A61B 8/08* | (2006.01) |
| *A61B 8/00* | (2006.01) |
| *G06T 7/00* | (2017.01) |

(52) U.S. Cl.
CPC .......... *A61B 8/0825* (2013.01); *A61B 8/4254* (2013.01); *A61B 8/4263* (2013.01);
(Continued)

(58) Field of Classification Search
CPC ... G06T 7/0014; A61B 8/0825; A61B 8/4254; A61B 8/4263; A61B 8/4427;
(Continued)

(56) References Cited

U.S. PATENT DOCUMENTS

2007/0239004 A1* 10/2007 Kakee .................. A61B 8/4245
                                                                    600/437
2015/0182191 A1    7/2015 Caluser et al.
(Continued)

FOREIGN PATENT DOCUMENTS

| JP | 06-066636 U | 9/1994 |
|---|---|---|
| JP | 2000-201926 A | 7/2000 |

(Continued)

OTHER PUBLICATIONS

Chinese Office Action dated Jun. 28, 2023, in Chinese Patent Application No. 202110371653.0, citing document 1, therein, 20 pages.

*Primary Examiner* — Joseph M Santos Rodriguez
*Assistant Examiner* — Brooke Lyn Klein
(74) *Attorney, Agent, or Firm* — Oblon, McClelland, Maier & Neustadt, L.L.P.

(57) ABSTRACT

According to one embodiment, an ultrasonic diagnostic apparatus includes processing circuitry. The processing circuitry is configured to acquire a current position information of an ultrasonic probe in three-dimensional space. The processing circuitry is further configured to switch from a body mark indicating one body part to a body mark indicating the other body part, when a body mark indicating one body part of a pair of left and right body parts is displayed, and when the ultrasonic probe is positioned at a position farther than a predetermined distance from a midpoint of the pair of left and right body parts toward the other body part.

2 Claims, 7 Drawing Sheets

(52) U.S. Cl.
CPC ............... *A61B 8/46* (2013.01); *A61B 8/466* (2013.01); *A61B 8/5207* (2013.01); *A61B 8/483* (2013.01); *A61B 8/58* (2013.01); *G06T 7/0014* (2013.01)

(58) Field of Classification Search
CPC ......... A61B 8/4472; A61B 8/46; A61B 8/466; A61B 8/468; A61B 8/483; A61B 8/488; A61B 8/5207; A61B 8/58
See application file for complete search history.

(56) References Cited

U.S. PATENT DOCUMENTS

| | | | |
|---|---|---|---|
| 2015/0305718 A1* | 10/2015 | Ogasawara | A61B 8/54 600/440 |
| 2018/0125459 A1 | 5/2018 | Oomori et al. | |
| 2021/0068782 A1* | 3/2021 | Caluser | A61B 8/461 |

FOREIGN PATENT DOCUMENTS

| | | | |
|---|---|---|---|
| JP | 2007-202829 A | 8/2007 | |
| JP | 2018-079301 A | 5/2018 | |

* cited by examiner

ULTRASONIC DIAGNOSTIC APPARATUS AND BODY MARK DISPLAY METHOD

CROSS-REFERENCE TO RELATED APPLICATIONS

This application claims the benefit of priority of Japanese Patent Application No. 2020-070295, filed Apr. 9, 2020, the entire contents of which are incorporated herein by reference.

FIELD

Embodiments described herein relate generally to an ultrasonic diagnostic apparatus and a body mark display method.

BACKGROUND

Some ultrasonic diagnostic apparatuses have a function to display an image called a body mark to indicate the imaging position.

The body mark is an image schematically showing the body part of the object. The user can easily grasp which body part is currently observed in the ultrasonic image by displaying the body mark together with the ultrasonic image generated based on the echo data acquired by the ultrasonic probe.

One technique for displaying the body mark is to use a position sensor to acquire the position information of the ultrasonic probe in the three-dimensional space (3D space), and to automatically display the body mark using the acquired position information. With this technique, based on the standard size and shape of the body part to be observed, the currently observed body part can be estimated from the position information of the ultrasonic probe, and the body mark corresponding to this body part can be automatically displayed.

However, with the technique that automatically displays the body mark based on the standard size and shape of the body part to be observed, it is very difficult for the user to know when to switch from one body mark to the other body mark when observing a pair of left and right body parts. For example, in this kind of technology, the midpoint of the two body parts is defined beforehand based on the standard size and shape of the two body parts, and the body mark switches to the other near the midpoint. In this case, when observing one body part of the pair of left and right body parts, the displayed body mark may switch to the body mark of the other body part, even though the user does not intend.

For example, let us consider the case where the user is scanning the ultrasonic probe around the left breast to observe the left breast. When the ultrasonic probe unexpectedly crosses the midpoint of the left and right breast determined based on the standard size and shape of the two body parts, it will be misinterpreted as a change in the observation target from the left breast to the right breast, and the body mark will switch from the left breast body mark to the right breast body mark. In the technique that automatically displays the body mark based on the standard size and shape of the body part to be observed, the intended body mark may not be displayed when the size of the left and right body parts currently observed are different from the standard size. Therefore, the display of body marks for the convenience of the user may rather hinder the continuation of the inspection.

DETAILED DESCRIPTION

Hereinbelow, a description will be given of an ultrasonic diagnostic apparatus and a body mark display method according to embodiments of the present invention with reference to the drawings.

The ultrasonic diagnostic apparatus according to an embodiment has a function of displaying a body mark.

In general, according to one embodiment, an ultrasonic diagnostic apparatus includes processing circuitry. The processing circuitry is configured to acquire a current position information of an ultrasonic probe in three-dimensional space. The processing circuitry is further configured to switch from a body mark indicating one body part to a body mark indicating the other body part, when a body mark indicating one body part of a pair of left and right body parts is displayed, and when the ultrasonic probe is positioned at a position farther than a predetermined distance from a midpoint of the pair of left and right body parts toward the other body part.

Figure 1:
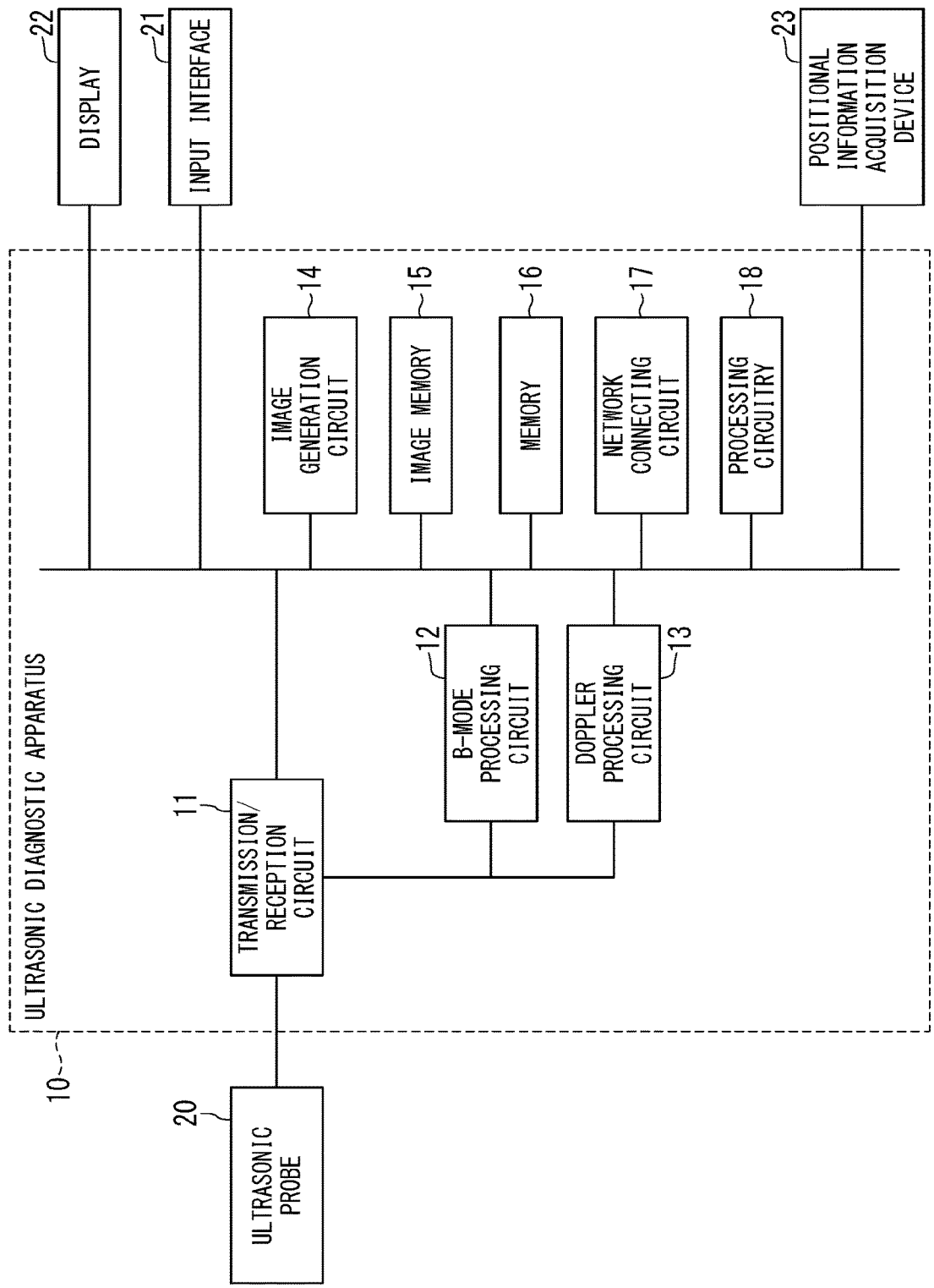
FIG. 1 is a block diagram illustrating a configuration example of an ultrasonic diagnostic apparatus according to an embodiment.

FIG. 1 is a block diagram illustrating a configuration example of an ultrasonic diagnostic apparatus 10 according to an embodiment.

The ultrasonic diagnostic apparatus 10 can be used in connection with an ultrasonic probe 20, an input interface 21, a display 22, and a positional information acquisition device 23. The ultrasonic diagnostic apparatus 10 may include at least one of the ultrasonic probe 20, the input interface 21, the display 22, and the positional information acquisition device 23. The ultrasonic diagnostic apparatus 10 may be a tablet type or a smart phone type.

The ultrasonic diagnostic apparatus 10 may have at least one of transmission/reception circuit 11, a B-mode processing circuit 12, a Doppler processing circuit 13, an image generation circuit 14, an image memory 15, a memory 16, a network connecting circuit 17, and processing circuitry 18 as shown in FIG. 1.

The transmission/reception circuit 11 includes a transmitting circuit and a receiving circuit.

The transmission/reception circuit 11 is controlled by the processing circuitry 18 to control the transmission directionality and reception directionality in transmission and reception of ultrasonic waves. FIG. 1 shows an example where the transmission/reception circuit 11 is installed in the ultrasonic diagnostic apparatus 10, but the transmission/reception circuit 11 may be installed in the ultrasonic probe 20, or in both the ultrasonic diagnostic apparatus 10 and the ultrasonic probe 20.

The transmitting circuit includes circuit elements such as a pulse generator, a transmission delay circuit, and a pulsar circuit, and supplies the ultrasonic transducers with a driving signal. The pulse generator repeatedly generates a rate pulse for forming a transmission ultrasonic wave at a predetermined rate frequency. The transmission delay circuit provides each rate pulse generated by the pulse generator with a delay time, which is separately determined for each ultrasonic transducer and is necessary for converging ultrasonic waves generated by the ultrasonic transducers into an ultrasonic beam and determining transmission directivity. Additionally, the pulsar circuit applies a driving pulse to the ultrasonic transducers at timing on the basis of each rate pulse. The transmission delay circuit appropriately adjusts a transmission direction of an ultrasonic beam transmitted from the ultrasonic transducer plane by changing the delay time provided to each rate pulse.

The receiving circuit includes circuit elements such as an amplifier circuit, an A/D converter, and an adder circuit. The receiving circuit receives echo signals received by the ultrasonic transducers, and generates echo data by performing various types of processing on the echo signals. The amplifier circuit performs gain correction processing on the echo signals by amplifying the echo signals for each channel. The A/D converter performs A/D conversion on the echo signals subjected to the gain correction processing, and provides the digitized data of the echo signals with each delay time necessary for determining reception directivity. The adder circuit performs addition processing of the echo signals digitized by the A/D converter so as to generate echo data. The addition processing performed by the adder circuit enhances each reflected component from a direction in accordance with reception directivity of each echo signal.

The B-mode processing circuit 12 receives the echo data from the receiving circuit and performs predetermined processing such as logarithmic amplification and envelope detection on the echo data so as to generate B-mode data in which signal intensity is indicated by brightness.

The Doppler processing circuit 13 performs frequency analysis on velocity information included in the echo data received from the receiving circuit, and extracts a blood-flow component, a tissue component, and a contrast-agent echo component by the Doppler Effect. In this manner, the Doppler processing circuit 13 generates Doppler data in which moving-object information items such as average velocity, variance, and power are extracted for multiple points.

The image generation circuit 14 generates ultrasonic image data based on echo signals received by the ultrasonic probe 20. For instance, the image generation circuit 14 generates two-dimensional B-mode image data, in which intensity of a reflected wave is indicated by brightness, from two-dimensional B-mode data generated by the B-mode processing circuit 12. Additionally, the image generation circuit 14 generates image data of a two-dimensional color Doppler image indicative of moving-object information from two-dimensional Doppler data generated by the Doppler processing circuit 13 in such a manner that the two-dimensional color Doppler image is generated as an average velocity image, a variance image, a power image, or a combination image of these images.

The image memory 15 is a memory configured to store data of images generated by the processing circuitry 18. The memory 16 has a configuration that includes a storage medium that can be read by a processor, such as a magnetic or optical storage medium or a semiconductor memory. Some or all of the programs and data in the memory 16 may be downloaded by communication over a network or may be given to the memory 16 via a portable storage medium such as an optical disk. Some or all of the information stored in the memory 16 may be distributed or mirrored in at least one of the storage media, such as an external memory or a memory not shown in the figure of the ultrasonic probe 20.

The network connecting circuit 17 implements various protocols for information and communication corresponding to a form of a network. The network connecting circuit 17 may connect the ultrasonic diagnostic apparatus 10 to other electrical equipment using the various protocols. This connection can be an electrical connection through an electronic network, etc. The network here means information and communications networks in general which use telecommunications technology and includes a wireless/wired LAN of a hospital's main LAN (Local Area Network), the Internet, a telephone line network, an optical fiber communications network, a cable communications network, and a satellite communications network.

The processing circuitry 18 realizes the function of general control of the ultrasonic diagnostic apparatus 10. The processing circuitry 18 is a processor that reads and executes the body mark display program stored in the memory 16 to appropriately display the user's intended body mark without using information on the size or shape of the body part.

The ultrasonic probe 20 is detachably connected to the ultrasonic diagnostic apparatus 10 via a cable. The ultrasonic probe 20 may also be wirelessly connected to the ultrasonic diagnostic apparatus 10.

The ultrasonic probe 20 may be a two-dimensional array probe in which a plurality of ultrasonic transducers is arranged in the scan direction (azimuth direction) and a plurality of elements are also arranged in the lens direction (elevation direction). For example, a 1.5D array probe, a 1.75D array probe, or a 2D array probe can be used as this type of 2D array probe.

The ultrasonic probe 20 may be configured to acquire volume data. In this case, the ultrasonic probe 20, which is a 2D array probe, may scan the object in 3D, or the ultrasonic probe 20, which is a 1D ultrasonic probe with multiple piezoelectric transducers arranged in a row, may scan the object in 2D, or the object can be scanned in three dimensions by rotating these multiple 1D ultrasonic transducers, or the multiple piezoelectric transducers of the 1D ultrasonic probe can be mechanically oscillated.

When the ultrasonic probe 20 is capable of acquiring volume data, the user can select either a two-dimensional display mode (2D mode) in which one of the multiple 2D ultrasonic images is displayed as a real-time movie or as a still image, or a four-dimensional display mode (4D mode) in which a 3D ultrasonic image being acquired in real-time is displayed as a movie.

The input interface 21 is realized by general input devices such as trackballs, switches, buttons, mouse, keyboards, touchpads for inputting operations by touching the operation surface, non-contact input circuits using optical sensors, audio input circuits and the like, and outputs the operation input signals corresponding to user operations to the processing circuitry 18. The input interface 21 may be configured as an operation panel. In this case, the operation panel functions as a touch command screen and has, for example, a display, a touch input circuit provided in the vicinity of the display, and hard keys.

The display 22 is composed of a general display output device, such as a liquid crystal display or an OLED (Organic Light Emitting Diode) display, for example, and displays various information according to the control of the processing circuitry 18. The ultrasonic diagnostic apparatus 10 may not include at least one of the input interface 21 and the display 22.

When the ultrasonic diagnostic apparatus 10 is a stationary device that includes the input interface 21 and the display 22, the input interface 21 may function as a touch command screen. When the ultrasonic diagnostic apparatus 10 is a tablet type or smartphone type ultrasonic diagnostic apparatus 10, the input interface 21 and the display 22 may constitute a touch panel as a single unit.

The positional information acquisition device 23 can be configured using, for example, a magnetic sensor, an infrared sensor, an optical sensor, or an acceleration sensor as a positional sensor. For example, when the positional information acquisition device 23 includes an optical sensor (e.g., an optical camera) as a positional sensor, the position information of the ultrasonic probe 20 is obtained based on the image data acquired by the optical camera installed at a position (e.g., ceiling or wall surface) where the ultrasonic probe 20 can be taken.

In addition, the positional information acquisition device 23 obtains the position information of the ultrasonic probe 20 based on the images of the marker from multiple directions taken by multiple optical cameras when the marker is installed on the housing of the ultrasonic probe 20. In this case, it is preferable that the distance between the marker and the transducer array surface or the distance between the marker and the predetermined position of the housing of the ultrasonic probe 20 be stored in memory 16 as offset information in advance.

When the positional information acquisition device 23 has a transmitter, a magnetic sensor as a position sensor, and a control unit, then the transmitter transmits a reference signal. Specifically, the transmitter is placed at a certain position and forms a magnetic field outward around the transmitter. The magnetic sensor as a position sensor acquires position information in the three-dimensional space by receiving the reference signal. The magnetic sensor as a position sensor is, for example, attached to the surface of the ultrasonic probe 20, detects the three-dimensional magnetic field formed by the transmitter, converts the information of the detected magnetic field into a signal, and outputs it to the control unit.

In this case, the control unit calculates the coordinates and orientation of the magnetic sensor in the three-dimensional coordinates with the transmitter as the origin based on the signals received from the magnetic sensor, and outputs the calculated coordinates and orientation to the processing circuitry 18 as position information of the ultrasonic probe 20.

Figure 2:
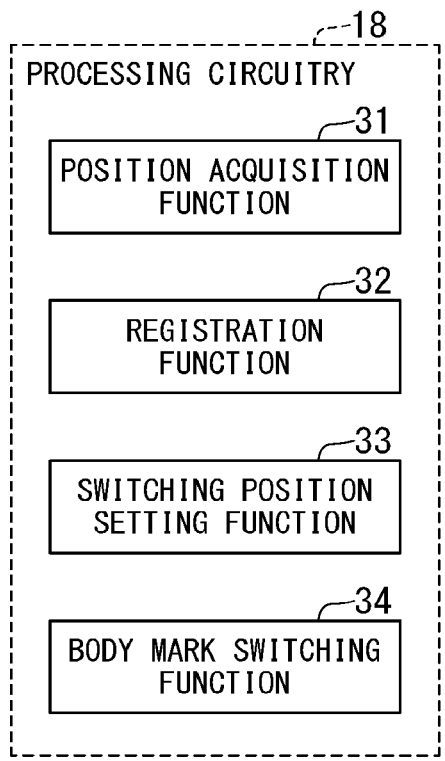
FIG. 2 is a schematic block diagram illustrating an example of functions implemented by a processor of a processing circuitry.

FIG. 2 is a schematic block diagram illustrating an example of functions implemented by a processor of a processing circuitry 18. As shown in FIG. 2, the processor of processing circuitry 18 realizes a position acquisition function 31, a registration function 32, a switching position setting function 33, and a body mark switching function 34. Each of these functions 31-34 is stored in the memory 16 in the form of a program.

The processor of the processing circuitry 18 appropriately displays the body mark indicating the corresponding body part that the user currently intends to observe without using the size or shape of the body parts, even when the left and right body parts as a pair are observed alternately.

Various body parts are known as the pair of left and right body parts, such as the breasts consisting of the left breast and the right breast, and the carotid arteries. The ultrasonic diagnostic apparatus 10 and the body mark display method according to the embodiment are applicable to any of these body parts. In the following description, an example is given where the pair of left and right body parts are the breasts.

Figures 3A, 3B:
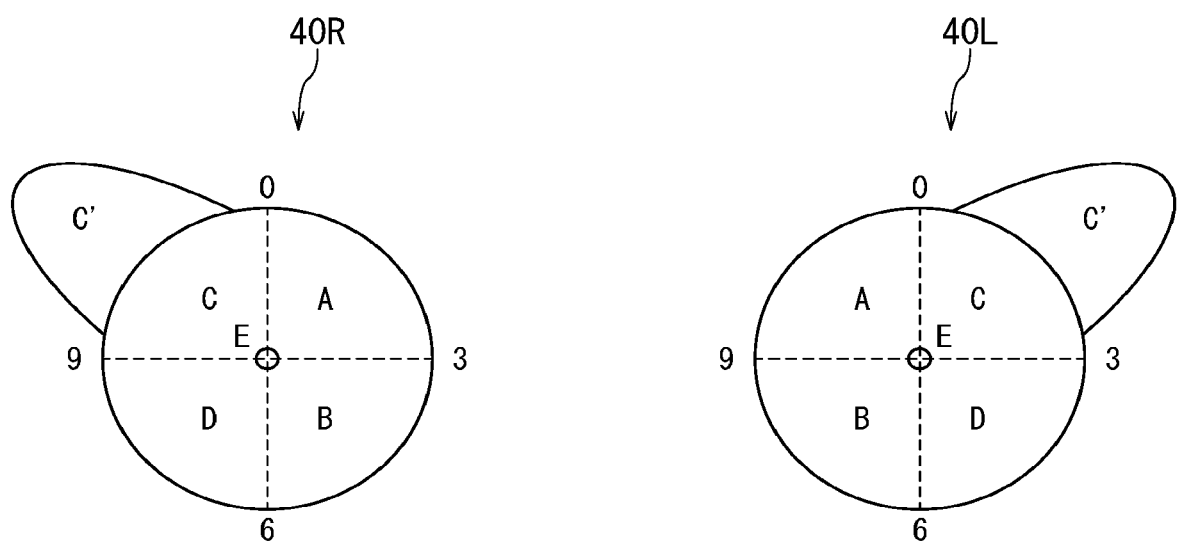
FIG. 3A is an explanatory drawing showing an example of a body mark indicating the right breast.
FIG. 3B is an explanatory drawing showing an example of a body mark indicating the left breast.

FIG. 3A is an explanatory drawing showing an example of the body mark 40R indicating the right breast. FIG. 3B is an explanatory drawing showing an example of the body mark 40L indicating the left breast.

In each of the body marks 40R indicating the right breast and 40L indicating the left breast, the numbers (0, 3, 6, 9) on the circumference indicate the azimuth in a clock with the nipple position as a center. The azimuth direction may be identified as a clockwise direction, with the vertical upward direction from the nipple position defined as the 0 o'clock (0 degree) azimuth when the object is in the standing position (see FIG. 3A and FIG. 3B).

A plurality of regions may be defined for each of the body marks 40R and 40L with the nipple position as a reference position. The plurality of regions may include, for example, fan-shaped A to D regions with a 90-degree angle each aligned around the nipple position, and a circular region E around the nipple position. The region E may also be classified into the areola region E and the nipple region E'. As to the A to D regions, in the case of body mark 40R, which indicates the right breast, the A to D regions may be defined in order in the counterclockwise direction when viewed from the front, while in the case of body mark 40L, which indicates the left breast, the A to D regions may be defined in order in the counterclockwise direction when viewed from the front. A region C' indicating the axillary region may be defined for each of the body marks 40R and 40L (see FIG. 3A and FIG. 3B).

The position acquisition function 31 acquires the current position information of the ultrasonic probe 20 in 3D space from the positional information acquisition device 23. The position acquisition function 31 may acquire the output signal of the positional sensor of the positional information acquisition device 23 and calculates the current position of the ultrasonic probe 20 based on the output signal of the positional sensor to acquire the current position information of the ultrasonic probe 20 in 3D space.

It is necessary to align the position of the ultrasonic probe 20 in 3D space with the body marks indicating each of the pair of left and right body parts in advance in order to automatically and appropriately switch the body marks according to the position of the ultrasonic probe 20 in 3D space.

Figure 4:
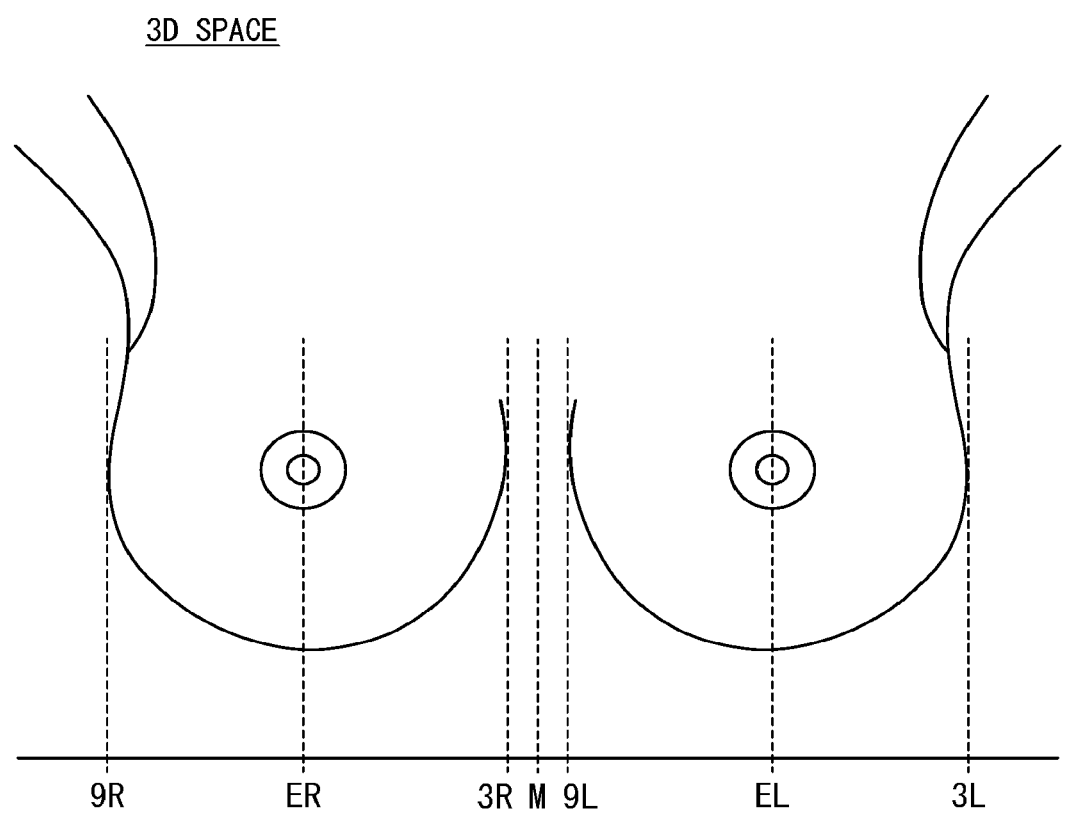
FIG. 4 is an explanatory diagram showing an example of the relationship between the positions of the left and right breasts in the 3D space and the positions of the reference points of the body mark indicating the right breast and the body mark indicating the left breast.
Figure 5:
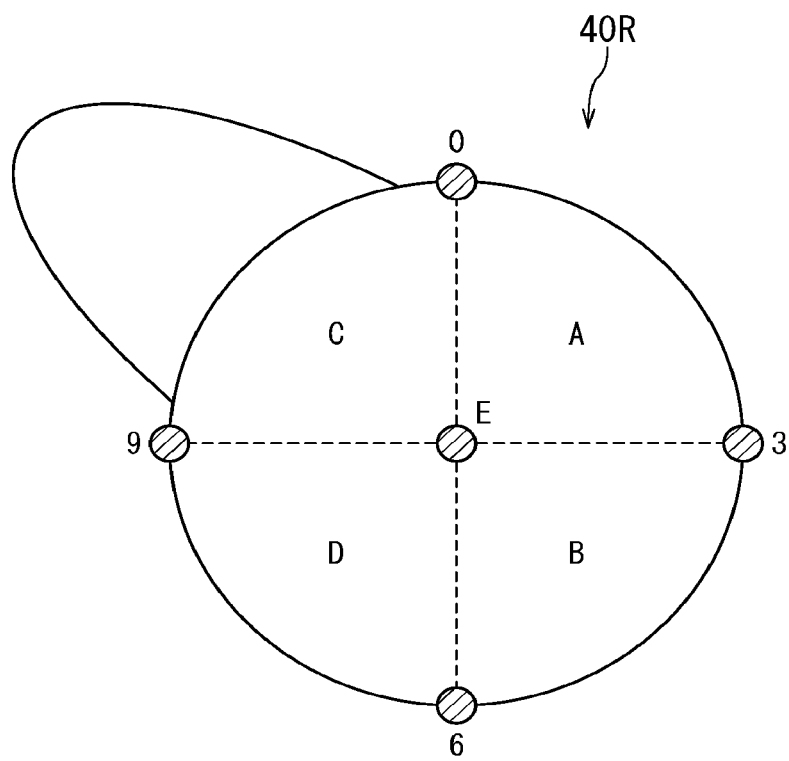
FIG. 5 is a diagram for explaining the alignment between the position of the ultrasonic probe in the 3D space and the body mark indicating the right breast.

FIG. 4 is an explanatory diagram showing an example of the relationship between the positions of the left and right breasts in the 3D space and the positions of the reference points of the body mark 40R indicating the right breast and the body mark 40L indicating the left breast. FIG. 5 is a diagram for explaining the alignment between the position of the ultrasonic probe 20 in the 3D space and the body mark 40R indicating the right breast.

The reference points include at least the nipple as the main reference point. The following is an example of a case where the reference points include not only the nipple but also the positions corresponding to 0, 3, 6, and 9 o'clock on the circumference of the body mark. In FIG. 5, the reference points of the right breast are shown as five small circles with shaded hatching. For the reference points of the right breast, the nipple shall be ER and the reference points on the circumference shall be marked with R for the number of the orientation (for example, the 3 o'clock position on the circumference of the body mark 40R is 3R), and for the reference points of the left breast, the nipple shall be EL and the reference points on the circumference shall be marked with L for the number of the orientation (see FIG. 4).

The registration function 32 aligns the ultrasonic probe 20 with the body marks that indicate each of the pair of left and right body parts (initial alignment (initial registration)). Specifically, the registration function 32 aligns the ultrasonic probe 20 with the body mark indicating one body part and the body mark indicating the other body part by associating the position in 3D space of the ultrasonic probe 20 with a position on the body mark of at least one reference point of one body part of the pair of left and right body parts and a position on the body mark of at least one reference point of the other body part.

For example, the user firstly positions the ultrasonic probe 20 at the position of the nipple of the right breast in 3D space, and instructs via the input interface 21 that the current position of the ultrasonic probe 20 in 3D space is the position corresponding to the right nipple ER of the body mark 40R. (See ER in FIG. 4). Similarly, the user indicates via the input interface 21 that the current position of the ultrasonic probe 20 in 3D space corresponds to the left nipple EL of the body mark 40L, while the ultrasonic probe 20 is positioned at the nipple position of the left breast in 3D space. (See EL in FIG. 4).

As a result, the registration function 32 is able to associate the position in 3D space of the ultrasonic probe 20 with the position on the body mark for each of the nipple ER of the right breast and the nipple EL of the left breast. Based on the information of at least these two main reference points, the registration function 32 can align the ultrasonic probe 20 with the body mark 40R indicating the right breast and the body mark 40L indicating the right breast. The registration function 32 may use multiple reference points for the left and right body parts, respectively.

The switching position setting function 33 automatically sets the position that is a predetermined distance away from the midpoint M of the pair of left and right body parts toward the other body part as the switching position, based on the positional relationship, obtained by alignment by the registration function 32, between the position of the ultrasonic probe 20 in 3D space, the position of at least one reference point on the body mark indicating one body part, and the position of at least one reference point on the body mark indicating the other body part. For example, the switching position setting function 33 automatically sets the position that is a predetermined distance away from the midpoint M of the main reference point of one body part and the main reference point corresponding to said main reference point of the other body part to the switching position. The predetermined distance does not include zero.

When the pair of left and right body parts are the left breast and the right breast, the switching position setting function 33 automatically sets the switching position ThLR for switching from the left breast to the right breast to a position that is a predetermined distance away from the midpoint M to the right breast side. The switching position ThLR is, for example, the nipple ER of the right breast. The switching position ThLR may be a predetermined position between 3R and ER (for example, the midpoint between 3R and ER), or a predetermined position between ER and 9R (for example, the midpoint between ER and 9R). Similarly, the switching position setting function 33 sets the switching position ThRL for switching from the right breast to the left breast to a position that is a predetermined distance away from the midpoint M to the left breast side.

In this way, the switching position setting function 33 can automatically set the switching position based on the alignment information about the reference point, without using the information about the size and shape of the body part. The switching position setting function 33 may display the candidates for the switching position on the display 22, and the user may select the switching position from the candidates.

The body mark switching function 34 switches from the body mark indicating one body part to the body mark indicating the other body part when the body mark indicating one body part of the pair of left and right body parts is displayed, and when the ultrasonic probe 20 is positioned at position that is a predetermined distance away from the midpoint M of the pair of left and right body parts to the other body part.

Figure 6:
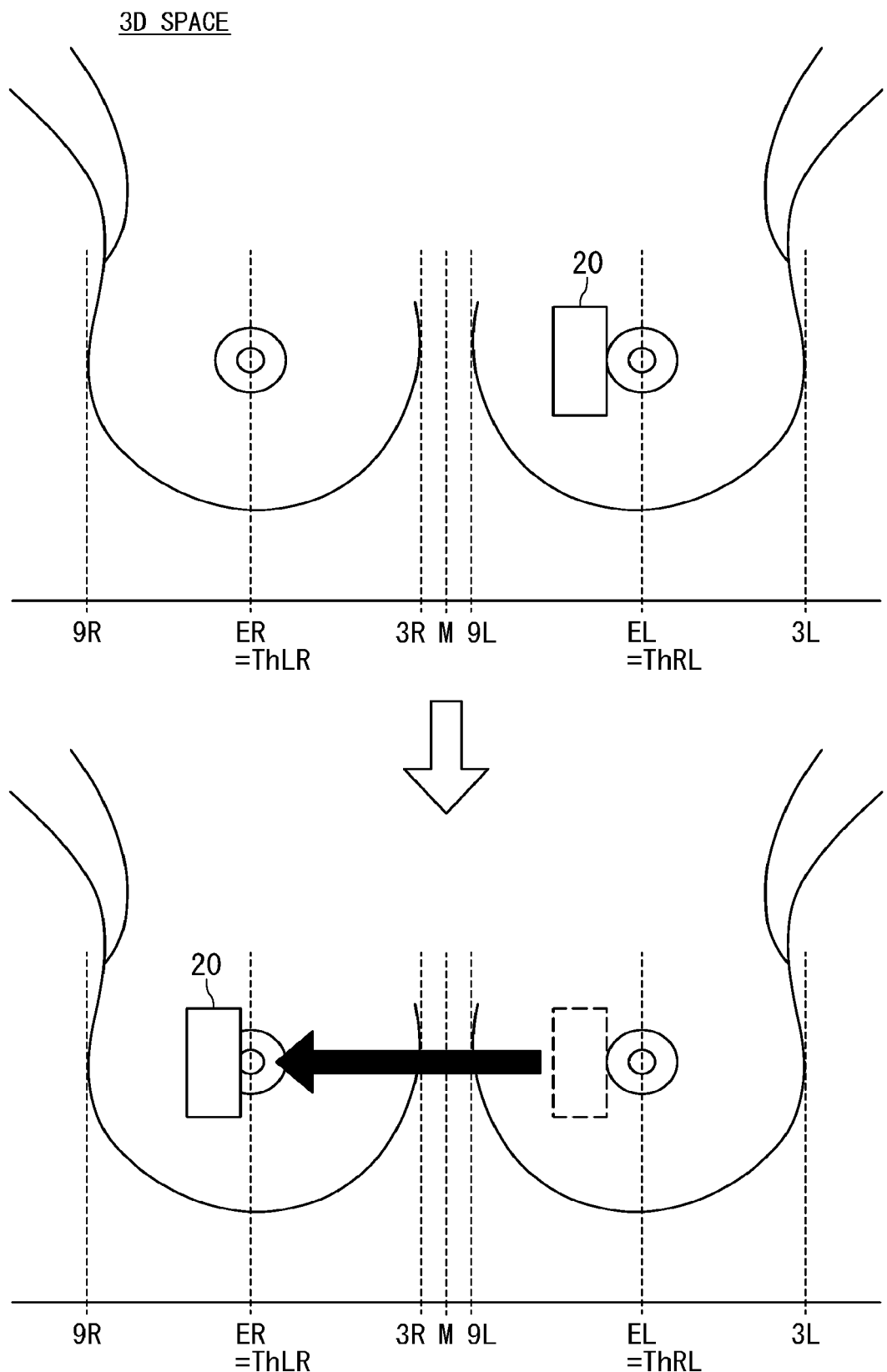
FIG. 6 is an explanatory diagram showing an example of a case where the ultrasonic probe moves from a position near the nipple of the left breast to a position farther away from the left breast than the nipple of the right breast.

FIG. 6 is an explanatory diagram showing an example of a case where the ultrasonic probe 20 moves from a position near the nipple EL of the left breast to a position farther from the left breast than the nipple ER (see left side of ER in FIG. 6) of the right breast. FIG. 6 shows an example of a case where the switching position ThRL for switching from the right breast to the left breast coincides with the nipple EL of the left breast and the switching position ThLR for switching from the left breast to the right breast coincides with the nipple ER of the right breast.

Figure 7:
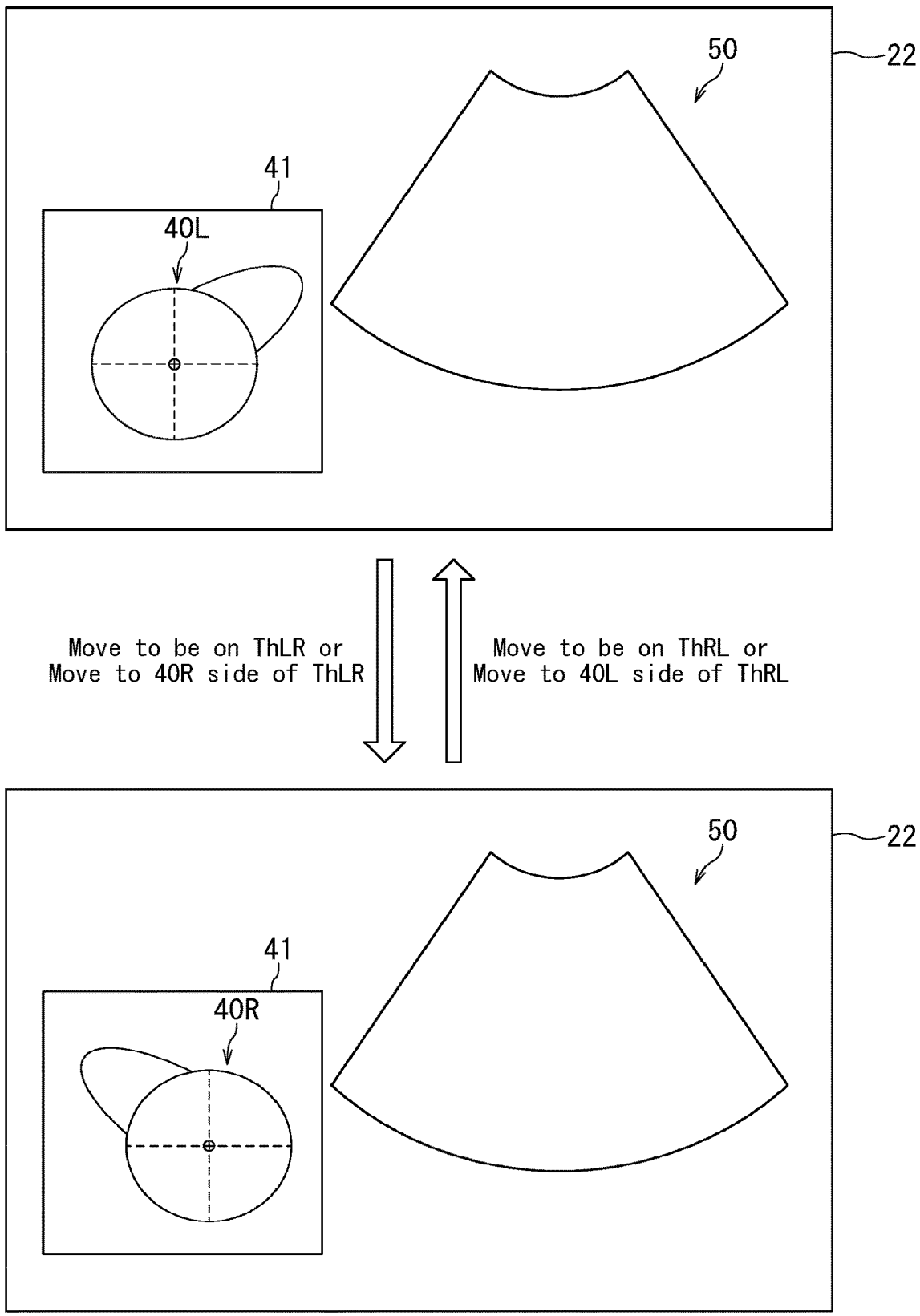
FIG. 7 is an explanatory diagram showing an example of how the body mark displayed in the body mark display area is switched in the example shown in FIG. 6.

FIG. 7 is an explanatory diagram showing an example of how the body mark displayed in the body mark display area 41 is switched in the example shown in FIG. 6.

Suppose the case where the display 22 displays the ultrasonic image 50 and also displays the body mark 40L indicating the left breast in the body mark display area 41 as shown in the upper part of FIG. 7. In this case, when the ultrasonic probe 20 is located at a position farther than a predetermined distance from the midpoint M to the right breast side (in the example of FIG. 6, at the nipple ER of the right breast, which is the switching position ThLR for switching from the left breast to the right breast, or farther from the left breast than the nipple ER), the body mark switching function 34 switches the body mark displayed in the body mark display area 41 from the body mark 40L indicating the left breast to the body mark 40R indicating the right breast (see the arrow from the top to the bottom of FIG. 7). After that, the ultrasonic probe 20 moves back to the left breast side, and when the ultrasonic probe 20 is located at a position farther than a predetermined distance away from the midpoint M to the left breast side (in the example of FIG. 6, it is located at the nipple EL of the left breast, which is the switching position ThRL for switching from the right breast to the left breast, or farther from the right breast than the nipple EL), the body mark switching function 34 switches the body mark displayed in the body mark display area 41 from the body mark 40R indicating the right breast to the body mark 40L indicating the left breast (see the arrow from the bottom to the top of FIG. 7).

Next, an example of the operation of the ultrasonic diagnostic apparatus and the body mark display method will be described.

Figure 8:
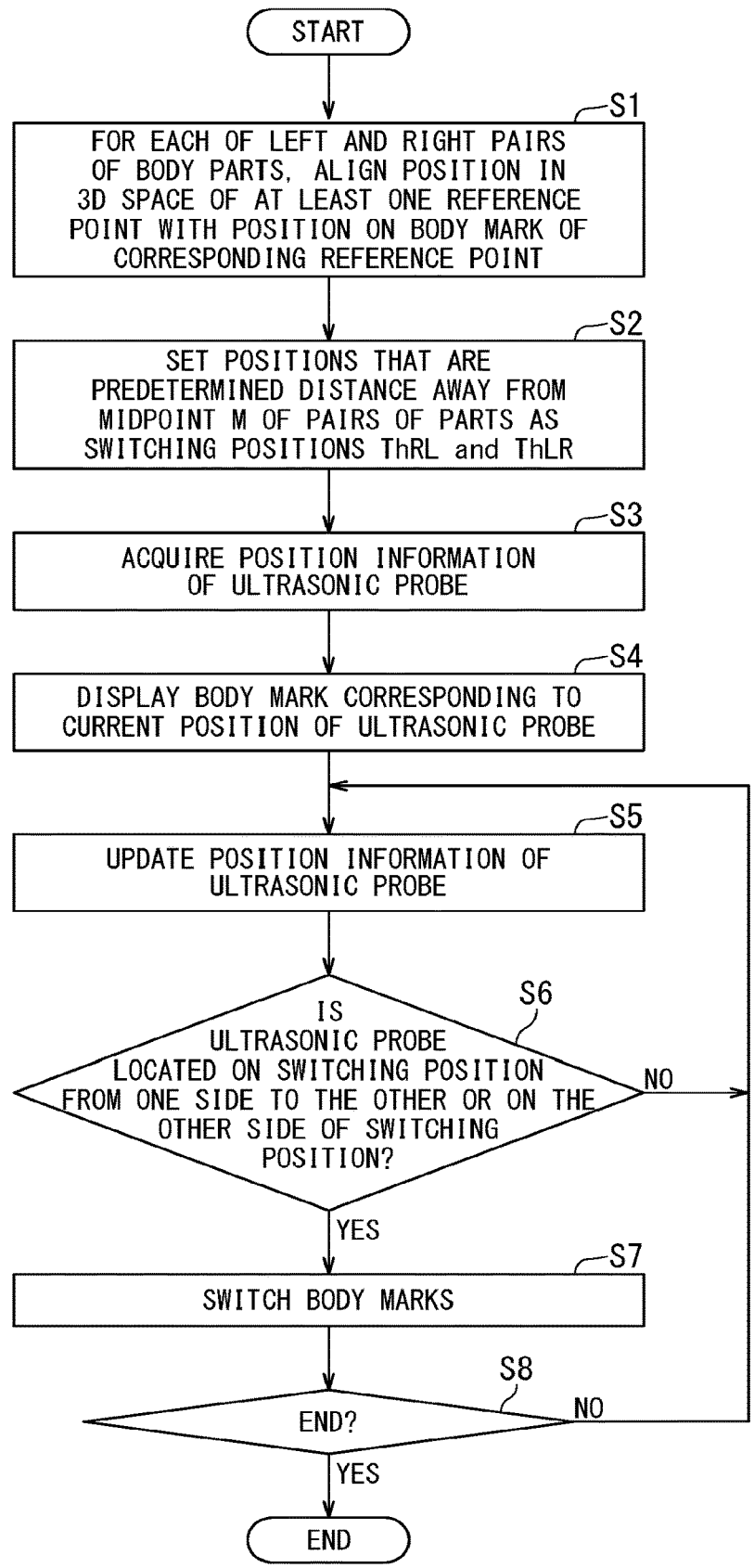
FIG. 8 is a flowchart showing an example of the procedure implemented by the processor of the processing circuitry shown in FIG. 1 to properly display the user's intended body mark when observing the pair of left and right body parts, without using information on the size or shape of the body part.

FIG. 8 is a flowchart showing an example of the procedure implemented by the processor of the processing circuitry 18 shown in FIG. 1 to properly display the user's intended body mark when observing the pair of left and right body parts, without using information on the size or shape of the body part. In FIG. 8, each reference sign composed of S and number on its right side indicates step number of the flowchart.

First, in step S1, the registration function 32 acquires the current position information of the ultrasonic probe 20 in the three-dimensional space from the position acquisition function 31. Then, the registration function 32 aligns the ultrasonic probe 20 with the body mark indicating one body part and the body mark indicating the other body part by associating the position in 3D space of the ultrasonic probe 20 with a position on the body mark of at least one reference point of one body part of the pair of left and right body parts and a position on the body mark of at least one reference point of the other body part (see FIGS. 4 and 5). Next, in step S2, the switching position setting function 33 automatically sets the position that is a predetermined distance away from the midpoint M of the pair of left and right body parts toward the other body part as the switching positions ThRL and ThLR, based on the alignment information obtained by the registration function 32.

Steps S1 and S2 may be performed before the ultrasonic scan of the object.

Next, when the ultrasonic scan of the object is started, in step S3, the position acquisition function 31 acquires the current position information of the ultrasonic probe 20 in the three-dimensional space.

Next, in step S4, the body mark switching function 34 displays the body mark corresponding to the current position of the ultrasonic probe 20 in the three-dimensional space.

Steps S3 and S4 are processes for determining the body mark initially displayed in the body mark display area 41, and the information on the switching positions ThRL and ThLR may not be used. For example, when a plurality of reference points is aligned with the ultrasonic probe 20 for each of the pair of left and right body parts, in step S4, the body mark switching function 34 may initially display a body mark indicating a body part corresponding to these multiple reference points when the current position in 3D space of the ultrasonic probe 20 is within the minimum circle encompassing these multiple reference points.

Next, in step S5, the body mark switching function 34 updates the current position information of the ultrasonic probe 20 in the three-dimensional space.

Next, in step S6, the body mark switching function 34 determines whether or not the ultrasonic probe 20 is located at a position that is a predetermined distance away from the midpoint M of the pair of left and right body parts toward the other body part, that is, the ultrasonic probe 20 is located on the switching position or on the other side of the switching position for switching from one body part to the other body part.

When the ultrasonic probe 20 is located closer to one body part than the position (switching position) that is a predetermined distance away from the midpoint M of the pair of left and right body parts to the other body part side (NO in step S6), the process returns to step S5. Meanwhile, when the ultrasonic probe 20 is located at or farther than a predetermined distance away from the midpoint M of the pair of left and right body parts to the other body part side (YES in step S6), the process proceeds to step S7.

Next, in step S7, the body mark switching function 34 switches the body mark displayed on the display 22 from the body mark indicating one body part to the body mark indicating the other body part (see FIG. 7).

Next, in step S8, the body mark switching function 34 determines whether the procedures should be ended according to an instruction to end the inspection or the like by the user. When it is determined that the procedures should be terminated, the series of procedures is terminated. Meanwhile, when it is determined that the process should not be terminated, the process returns to step S5.

According to the above procedure, when observing the pair of left and right body parts, the body mark indicating the corresponding body part that the user currently intends to observe can be appropriately displayed without using the size or shape of the body parts.

In the technology that automatically displays body marks based on the standard size and shape of the body parts to be observed, when observing one of the body parts of a pair of left and right body parts, the midpoint between the two body parts may be set as the body mark switching position. In such a case, when a user is scanning around the midpoint, an unintended body mark may often be displayed, or the body mark may be frequently switched, which is very inconvenient for the user.

The ultrasonic diagnostic apparatus 10 according to the embodiment aligns the ultrasonic probe 20 with the body mark, and switches the body mark using this alignment information. Specifically, the ultrasonic diagnostic apparatus 10 sets a position that is a predetermined distance away from the midpoint between the main reference points toward the other body part as the switching position based on the alignment information of each main reference point of the left and right body parts. Therefore, unless the ultrasonic probe 20 is moved to a position that is a predetermined distance away from the midpoint toward the other body part, the displayed body mark indicating one body part will not switch to the body mark indicating the other body part. Therefore, compared to the case where the switching position is set based on the shape and size of the body part, the body mark indicating the one body part can be reliably maintained when the one body part is being observed.

When the user wishes to observe the other body part, it is necessary to move the ultrasonic probe 20 significantly from the midpoint to a position that is a predetermined distance away from the midpoint toward the other body part. Hence, the user can switch to the body mark indicating the other body part by moving the ultrasonic probe 20 to the other side with a clear intention.

Accordingly, the ultrasonic diagnostic apparatus 10 can reliably display the body mark that indicates the body part intended to be observed by the user, regardless of the size and shape of the body part. As a result, the inspection time can be significantly shortened.

According to at least one of the above-described embodiments, the user's intended body mark can be properly displayed without using information on the size or shape of the body part.

The term "processor" used in the explanation in the above-described embodiments, for instance, refers to circuitry such as dedicated or general purpose CPUs (Central Processing Units), dedicated or general-purpose GPUs (Graphics Processing Units), or ASICs (Application Specific Integrated Circuits), programmable logic devices including SPLDs (Simple Programmable Logic Devices), CPLDs (Complex Programmable Logic Devices), and FPGAs (Field Programmable Gate Arrays), and the like. The processor implements various types of functions by reading out and executing programs stored in the memory circuitry.

In addition, instead of storing programs in the memory circuitry, the programs may be directly incorporated into the circuitry of the processor. In this case, the processor implements each function by reading out and executing each program incorporated in its own circuitry. Moreover, although in the above-described embodiments an example is shown in which the processing circuitry configured of a single processor implements every function, the processing circuitry may be configured by combining plural processors independent of each other so that each processor implements each function of the processing circuitry by executing the corresponding program. When a plurality of processors is provided for the processing circuitry, the memory medium for storing programs may be individually provided for each processor, or one memory circuitry may collectively store programs corresponding to all the functions of the processors.

While certain embodiments have been described, these embodiments have been presented by way of example only, and are not intended to limit the scope of the inventions. Indeed, the novel embodiments described herein may be embodied in a variety of other forms; furthermore, various omissions, substitutions, and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus, comprising:
processing circuitry configured to
acquire current position information of an ultrasonic probe in three-dimensional space;
align the ultrasonic probe with a first body mark indicating one breast of a pair of left and right breasts by associating first positions in three-dimensional space of the ultrasonic probe with corresponding positions of the one breast including a position of a nipple and 0, 3, 6, and 9 o'clock positions on a circumference of the one breast;
align the ultrasonic probe with a second body mark indicating another breast of the pair of left and right breasts by associating second positions in the three-dimensional space of the ultrasonic probe with corresponding positions of the another breast part including a position of a nipple and 0, 3, 6, and 9 o'clock positions on a circumference of the another breast; and
when the first body mark indicating the one breast is displayed, and when the processing circuitry determines that the ultrasonic probe reaches a position farther than a predetermined non-zero distance from a midpoint between the 3 o'clock position and the nipple of the another breast or a midpoint between the 9 o'clock position and the nipple of the another breast toward the another breast, switch from displaying the first body mark indicating the one breast to displaying the second body mark indicating the another breast.

2. A body mark display method, comprising:
acquiring, by processing circuitry, a current position information of an ultrasonic probe in three-dimensional space;
aligning the ultrasonic probe with a first body mark indicating one breast of a pair of left and right breasts by associating first positions in three-dimensional space of the ultrasonic probe with corresponding positions of the one breast including a position of a nipple and 0, 3, 6, and 9 o'clock positions on a circumference of the one breast;
aligning the ultrasonic probe with a second body mark indicating another breast of the pair of left and right breasts by associating second positions in the three-dimensional space of the ultrasonic probe with corresponding positions of the another breast part including a position of a nipple and 0, 3, 6, and 9 o'clock positions on a circumference of the another breast;
displaying indicating another breast;
determining that the ultrasonic probe reaches a position farther than a predetermined non-zero distance from a midpoint between the 3 o'clock position and the nipple of the another breast or a midpoint between the 9 o'clock position and the nipple of the another breast toward the another breast, and in response, switching from displaying the first body mark indicating the one breast to displaying the second body mark indicating the another breast.

* * * * *